United States Patent [19]

Boriack et al.

[11] 4,377,707

[45] Mar. 22, 1983

[54] HALOGENATED (METH) ACRYLATE COMPOUNDS

[75] Inventors: Clinton J. Boriack, Freeport; Hans R. Friedli, Lake Jackson, both of Tex.

[73] Assignee: The Dow Chemical Company, Midland, Mich.

[21] Appl. No.: 331,748

[22] Filed: Dec. 17, 1981

[51] Int. Cl.$^3$ ............... C07C 69/54; C07C 69/63; C07C 153/09
[52] U.S. Cl. .................. 560/220; 560/228; 260/455 R
[58] Field of Search ............... 560/220, 228; 260/455 R; 526/282

[56] References Cited

U.S. PATENT DOCUMENTS 3,143,535 8/1964 Jackson et al. ............... 560/220
4,097,677 6/1978 Emmons et al. ............... 560/220

Primary Examiner—Natalie Trousof
Assistant Examiner—L. Hendriksen
Attorney, Agent, or Firm—B. G. Colley

[57] ABSTRACT

Halogenated dicyclopentyl ethers or thioethers of alkylene glycol mono(meth) acrylate or mono (meth) propionates are prepared. The dihalo compounds having (meth) acrylic functionality are useful to prepare thermosetting or thermoplastic resins with built in fire retardency. The tetrahalo compounds are useful fire retardant additives in the manufacture of polymeric foams.

12 Claims, No Drawings

HALOGENATED (METH) ACRYLATE COMPOUNDS

BACKGROUND OF THE INVENTION

This invention relates to new compounds such as (dihalodicyclopentyl-5 or 6-oxy)-substituted (meth) acrylates and the related dihalopropionates.

From U.S. Pat. No. 3,143,535, dated Aug. 4, 1964, it is known that 2,3-dibromodicyclopentyl (meth) acrylates can be prepared.

The compounds of this invention having (meth) acrylic functionality are useful to prepare thermosetting or thermoplastic resins with built in fire retardency. These compounds are highly reactive under ultraviolet and electron beam curing conditions. On the other hand, the tetrahalo compounds having no unsaturation are useful as fire retardant additives in the manufacture of polymeric foams such as polystyrene and polyurethane.

SUMMARY OF THE INVENTION

The compounds of this invention have the formulae

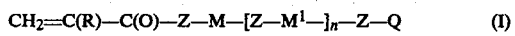

$$CH_2=C(R)-C(O)-Z-M-[Z-M^1-]_n-Z-Q \quad (I)$$

$$CH_2(X)-C(R)(X)-C(O)-Z-M-[Z-M^1-]_n-Z-Q \quad (II)$$

where
Q is the 2,3-dihalodicyclopentyl group

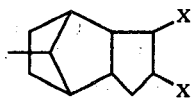

X is chlorine or bromine
R is hydrogen or methyl
M is an alkylene group having 2-10 carbon atoms
M¹ is an alkylene group having 2-10 carbon atoms and can be the same as or different from M
Z is oxygen or sulfur
n is zero to three The compound of Formulae I and II can be named in various ways. For example in I where n is zero, R is hydrogen, Z is oxygen, M is ethylene and x is bromine it can be called 2-(2,3-dibromo-2,3,3a,4,5,6,7,7a-octahydro-4,7-methano-1H-indan-5 or 6-oxy)ethyl-2-propenoate using the indenyl nomenclature. It can also be named 2-(3,4-dibromo-tricyclo[5.2.1.0$^{2,6}$]decyl-8 or 9-oxy) ethyl-2-propenoate using the tricyclo nomenclature. For reasons of simplicity, the compounds of this invention will be named hereinafter on the basis of their derivation from dicyclopentadiene.

DETAILED DESCRIPTION

The compounds of this invention are prepared by the bromination or chlorination of the starting material. It is preferred to use a solvent during the halogenation reaction.

The starting materials for this invention have the generic formula

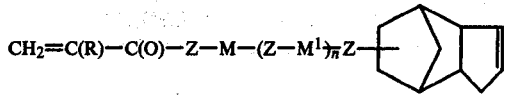

$$CH_2=C(R)-C(O)-Z-M-(Z-M^1)_n Z-$$

where
R is hydrogen or methyl
M and M¹ are alkylene groups of 2-10 carbon atoms
Z is oxygen or sulfur
n is 0 to 3.

They can be prepared by esterification of a glycol monodicyclopentenyl ether or a polyalkylene glycol monodicyclopentenyl ether or thioether with (meth) acrylic acid.

The glycol monodicyclopentenyl ether or thioether have the generic formula

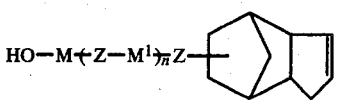

$$HO-M-(Z-M^1)_n Z-$$

where M, Z, n, and M¹ have the same meanings as above.

Examples of glycols useful to make the above monoethers are ethylene glycol, propylene glycol, 1,4-butanediol, 1,5-pentanediol, neopentyl glycol, 1,6-hexanediol, 1,8-octanediol and the corresponding thiodiols or mixed glycol-thiols such as ethandithiol and thiodiethanol.

Examples of polyalkylene glycols useful to make the above monoethers are thiodiethanol, diethylene glycol, triethylene glycol, tetraethylene glycol, dipropylene glycol, tripropylene glycol, and tetaethylene glycol.

Some of the above starting materials and a method for their production are shown in U.S. Pat. No. 4,097,677 dated June 27, 1978. This patent is incorporated by reference herein.

The unsaturated starting materials may be dissolved in a solvent such as methylene chloride, carbon tetrachloride, chloroform, methylchloroform, fluorocarbons, such as the Freons ®, e.g., Freon 11, 12, 21, 114, and benzene or they may be halogenated without the use of solvent. The amount of solvent used can vary from 50 to 90 volume percent of the solution to be reacted.

The solution is then brominated with the incremental addition of liquid bromine at a temperature in the range from −30° to 50° C.

The amount of bromine added is about 0.5 to 1.1 moles per mole of unsaturation in the starting material.

For the corresponding chlorination reaction, gaseous chlorine is added to the solution at a temperature in the range from −30° to 50° C.

In order to make the tetrahalo compounds, (Formula II above) the dihalo compounds (Formula I) may be isolated and further treated in the above manner or they may be made without isolation of the dihalo compounds.

The following examples are presented to illustrate but not limit the invention.

EXAMPLE 1

To a 100 ml three neck flask fitted with a thermometer, addition funnel, and a calcium sulfate drying tube were added 25 ml of methylene chloride and 5 g (0.02 mol) of 2-(dicyclopentenyl-5-oxy) ethyl acrylate. This starting material was prepared by the method set forth in Example 2 of U.S. Pat. No. 4,097,677. The solution was stirred magnetically and cooled to −20° C. Then 3.2 g bromine (0.02 mol) was added dropwise. During addition of the bromine the temperature was maintained at −20° C. After all the bromine was added the solution was stirred at −20° until the intense red-brown color of the solution disappeared. The reaction solution was washed with aqueous sodium thiosulfate, distilled water, and dried over anhydrous magnesium sulfate. The dessicant was removed by filtration. To the filtrate was added 1% by weight (based on theoretical yield of product) each of styrene and t-butyl glycidyl ether as polymerization and color inhibitors. The solvents were removed in vacuo to give an oil which was identified by its spectral properties (infrared and proton magnetic resonance) as 2-(2,3-dibromodicyclopentyl-5-oxy) ethyl acrylate or the acrylate ester of ethylene glycol 2,3-dibromodicyclopentyl ether.

EXAMPLE 2

The same procedure as described in Example 1 was used except 5 g (19 mmol) of the corresponding methacrylate was reacted with 3.1 g (19 mmol) of bromine. The starting material was prepared by the method set forth in Example 1 of U.S. Pat. No. 4,097,677. The final product had spectral features which indicated bromine had added only to the cyclopentenyl double bond to give 2-(2,3-dibromodicyclopentyl-5-oxy)ethyl methacrylate or the methacrylate ester of ethylene glycol 2,3-dibromodicyclopentyl ether.

EXAMPLE 3

To a three neck 100 ml flask fitted with gas inlet tube, thermometer, and CaSO$_4$ drying tube were added 5 g (0.02 mol) of 2-(dicyclopentenyl-5-oxy) ethyl acrylate and 50 ml of CH$_2$Cl$_2$. The solution was stirred magnetically and the temperature lowered to −10° C.

Chlorine gas was added for a total of eight minutes at a rate of ~0.16 g/min. The reaction was followed by gas chromatography to determine when the substrate was completely reacted. The reaction product was washed three times with distilled water, dried over MgSO$_4$, and then filtered to remove the dessicant. To the filtrate was added ~2 mg of the monomethyl ether of hydroquinone. The solvent was removed under vacuum to give a dark green oil, which was identified by its spectral properties as 2-(2,3-dichlorodicyclopentyl-5-oxy)ethyl acrylate or the acrylate ester of ethylene glycol 2,3-dichlorodicyclopentyl ether.

EXAMPLE 4

The procedure described in Example 3 was used except 5 g of 2-(dicyclopentenyl-5-oxy)ethyl methacrylate was reacted at −20° C. with chlorine gas flowing at ~0.17 g/min for seven minutes. The product has spectral features which identified the compound as the 2-(2,3-dichlorodicyclopentyl-5-oxy)ethyl methacrylate or the methacrylate ester of ethylene glycol 2,3-dichlorodicyclopentyl ether.

EXAMPLE 5

A 100 ml three neck flask fitted with an addition funnel, thermometer and drying tube was charged with 5 g (0.02 mol) of the acrylate of Example 3 and 50 ml of CH$_2$Cl$_2$. The contents of the flask were stirred and cooled to 0° C. Bromine (6.4g, 0.04 mol) was added dropwise while maintaining the temperature at 0° C. After the bromine was added, the contents of the reactor were allowed to warm to room temperature. After one hour the product was washed once with aqueous Na$_2$S$_2$O$_3$, washed three times with distilled water, and dried with anhydrous MgSO$_4$. The MgSO$_4$ was removed by filtration and the filtrate concentrated under vacuum at 65° C. The product, a viscous, light yellow oil, had spectral properties which identified it as 2-(2,3-dibromodicyclopentyl-5-oxy)ethyl 2,3-dibromopropionate or the 2,3-dibromopropionate ester of 2,3-dibromodicyclopentyl ethylene glycol ether.

Results similar to the above examples are obtained when the ethylene glycol component is replaced by other glycols and polyalkylene glycols such as propylene glycol, diethylene glycol, dipropylene glycol and thiodiethanol.

We claim:

1. A compound having the formula

where

Q is the 2,3-dihalodicyclopentyl group

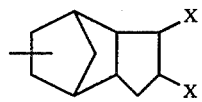

X is chlorine or bromine,
R is hydrogen or methyl,
M is an alkylene group having 2–10 carbon atoms,
M$^1$ is an alkylene group having 2–10 carbon atoms and can be the same as or different from M,
Z is oxygen or sulfur,
n is zero to three.

2. A compound having a formula

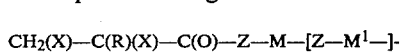

where

Q is the 2,3-dihalodicyclopentyl group

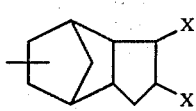

X is chlorine or bromine,
R is hydrogen or methyl,
M is an alkylene group having 2–10 carbon atoms,
M$^1$ is an alkylene group having 2–10 carbon atoms and can be the same as or different from M,
Z is oxygen or sulfur,
n is zero or three.

3. A compound having the formula

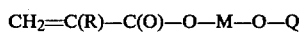

where

Q is the 2,3-dihalodicyclopentyl group

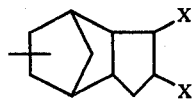

X is chlorine or bromine,
R is hydrogen or methyl,
M is an alkylene group having 2-10 carbon atoms.

4. A compound as defined in claim 3 wherein X is bromine, R is hydrogen and M is an ethylene group.

5. A compound as defined in claim 3 wherein X is chlorine, R is hydrogen and M is an ethylene group.

6. A compound as defined in claim 3 wherein X is bromine, R is methyl, and M is an ethylene group.

7. A compound as defined in claim 3 wherein X is chlorine, R is methyl and M is an ethylene group.

8. A compound having the formula

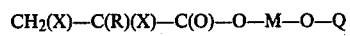
CH₂(X)—C(R)(X)—C(O)—O—M—O—Q where
Q is the 2,3-dihalodicyclopentyl group

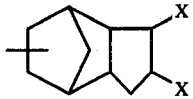

X is chlorine or bromine,
R is hydrogen or methyl,
M is an alkylene group having 2-10 carbon atoms.

9. A compound as defined in claim 8 wherein X is bromine, R is hydrogen, and M is an ethylene group.

10. A compound as defined in claim 8 wherein X is chlorine, R is hydrogen, and M is an ethylene group.

11. A compound as defined in claim 8 wherein X is bromine, R is methyl, and M is an ethylene group.

12. A compound as defined in claim 8 wherein X is chlorine, R is methyl, and M is an ethylene group.

* * * * *